United States Patent
Ushioda et al.

(10) Patent No.: US 8,680,110 B2
(45) Date of Patent: Mar. 25, 2014

(54) P2X₄ RECEPTOR ANTAGONIST

(75) Inventors: Masatoshi Ushioda, Misato (JP); Shogo Sakuma, Misato (JP); Toshiyasu Imai, Misato (JP); Kazuhide Inoue, Fukuoka (JP)

(73) Assignee: Nippon Chemiphar Co., Ltd., Tokyo (JP)

( * ) Notice: Subject to any disclaimer, the term of this patent is extended or adjusted under 35 U.S.C. 154(b) by 0 days.

(21) Appl. No.: 13/811,909

(22) PCT Filed: Jul. 27, 2011

(86) PCT No.: PCT/JP2011/067028
§ 371 (c)(1),
(2), (4) Date: Apr. 4, 2013

(87) PCT Pub. No.: WO2012/017876
PCT Pub. Date: Feb. 9, 2012

(65) Prior Publication Data
US 2013/0184459 A1 Jul. 18, 2013

(30) Foreign Application Priority Data
Aug. 3, 2010 (JP) ................. 2010-174240

(51) Int. Cl.
A61K 31/517 (2006.01)
A61K 31/519 (2006.01)
C07D 239/70 (2006.01)

(52) U.S. Cl.
USPC ......................... 514/267; 544/249

(58) Field of Classification Search
USPC .......................... 544/249; 514/267
See application file for complete search history.

(56) References Cited

U.S. PATENT DOCUMENTS

2005/0074819 A1    4/2005   Inoue et al.

*Primary Examiner* — Kristin Vajda
(74) *Attorney, Agent, or Firm* — Nixon Peabody LLP; Jeffrey L. Costellia

(57) ABSTRACT

A compound having the following formula (II) or a pharmacologically acceptable salt thereof is used as a P2X₄ receptor antagonist:

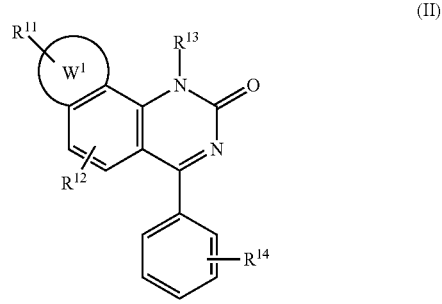

(II)

wherein each of $R^{11}$ and $R^{12}$ is hydrogen, $C_{1-8}$ alkyl or the like;
$R^{13}$ is hydrogen, $C_{1-8}$ alkyl or the like;
$R^{14}$ is $C_{1-8}$ alkoxy, hydroxyl, cyano, a heterocyclic group optionally having a substituent or the like; and
the condensed ring consisting of $W^1$ and the neighboring benzene ring is naphthalene ring or the like.

19 Claims, No Drawings

P2X4 RECEPTOR ANTAGONIST

FIELD OF THE INVENTION

The present invention relates to a diazepine derivative showing $P2X_4$ receptor antagonism.

BACKGROUND OF THE INVENTION

ATP receptors are basically classified into P2X family of ion-channel type receptors and P2Y family of G protein-coupled receptors. Until now, there are reported, respectively, seven sub-types ($P2X_{1-7}$) and eight sub-types ($P2Y_{1, 2, 4, 6, 11-14}$).

It has been reported that $P2X_4$ receptor (Genebank No. X87763), which is a sub-type of P2X family, is present widely in the central nervous systems (cf. Non-patent documents 1-5).

The mechanism of pathogenesis of intractable pains such as neuropathic pain is unclear. Therefore, if non-steroidal anti-inflammatory drugs (NSAIDs) and morphine are not effective, there is no other pharmacotherapy. In that case, the patient and surrounding people take up a heavy burden in mind and body. The neuropathic pain is caused by injury of peripheral or central nervous systems, for instance, post-surgery pain, cancer, spinal cord injury, herpes zoster, diabetic neuritis, or trigeminal neuralgia.

Recently, Inoue, et al. studied the involvement of P2X receptors in neuropathic pain using dorsal root ganglion neuron-injured animal model, which induces allodynia, and indicated that the nerve-injured pain (particularly, allodynia) is caused via $P2X_4$ receptors on spinal microglia (cf. Non-patent documents 6, 7, and Patent document 1).

Accordingly, compounds that inhibit the action of $P2X_4$ receptors are expected to be employed for preventing or treating nociceptive, inflammatory, and neuropathic pains.

Patent document 2 discloses that benzofuro-1,4-diazepin-2-one derivatives having the below-illustrated formula (A) show $P2X_4$ receptor antagonism:

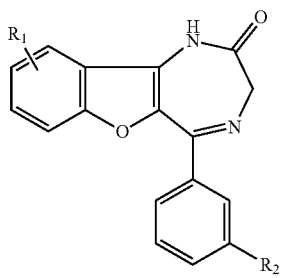

(A)

wherein $R_1$ is halogen, and $R_2$ is hydrogen, halogen, nitro, cyano, C(O)—$OR_3$, C(O)—$NR_4R_5$, $SO_2$—$OR_3$, or $SO_2$—$NR_4R_5$, or in which $R^1$ is hydrogen, and $R_2$ is halogen, nitro, cyano, C(O)—$OR_3$, C(O)—$NR_4R_5$, $SO_2$—$OR_3$, or $SO_2$—$NR_4R_5$.

Non-patent document 8 discloses that Paroxetine known as an antidepressant also shows $P2X_4$ receptor antagonism.

The present inventors have found that naphtho[1,2-e]-1,4-diazepin-2-one derivatives having the below-illustrated formula (B) showing $P2X_4$ receptor antagonism, and filed the Patent document 3.

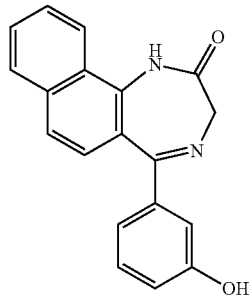

(B)

Patent document 4 describes that the compound having the quinazoline structure represented by the formula (C) shows an anti-inflammatory effect.

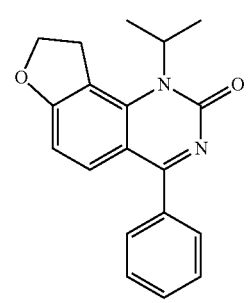

(C)

Non-patent document 9 describes a process for preparation of the compound having the quinazoline structure represented by the formula (D).

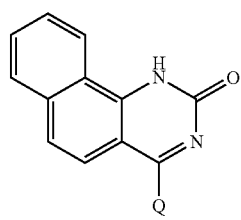

(D)

In the formula, Q is phenyl, p-methylphenyl, p-chlorophenyl, and thiophen-2-yl.

Patent document 4 and Non-patent document 9, however, do not describe that the compounds having the quinazoline structures represented by the formulas (C) and (D) have the $P2X_4$ receptor antagonism.

PRIOR ART DOCUMENTS

Patent Documents

Patent document 1: United States patent publication No. 20050074819
Patent document 2: WO 2004/085440
Patent document 3: WO 2008/023847
Patent document 4: U.S. Pat. No. 3,963,717

Non-Patent Documents

Non-patent document 1: Buell, et al. (1996) EMBO J. 15: 55-62
Non-patent document 2: Seguela, et al. (1996) J. Neurosci. 16: 448-455
Non-patent document 3: Bo, et al. (1995) FEBS Lett. 375: 129-133
Non-patent document 4: Soto, et al. (1996) Proc. Natl. Acad. Sci. USA 93: 3684-3788
Non-patent document 5: Wang, et al. (1996) Biochem. Res. Commun. 220: 196-202
Non-patent document 6: M. Tsuda, et al. (2003) Nature, 424, 778-783
Non-patent document 7: Jeffrey A. M. Coull, et al. (2005) Nature, 438, 1017-1021
Non-patent document 8: Paper Abstract of Lecture Program P3-N-114, The 49th Annual Meeting of Japanese Society for Neurochemistry (2006)
Non-patent document 9: Doklady Bolgarskoi Akademii Nauk (1987), 40(12), 41-4

SUMMARY OF THE INVENTION

Problems to be Solved by the Invention

It is the object of the present invention to provide a compound represented by the formula (I) or (II), which shows $P2X_4$ receptor antagonism.

Means for Solving the Problems

The present invention relates to a compound having the following formula (I) or a pharmacologically acceptable salt thereof:

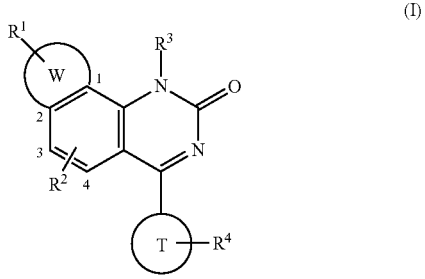

(I)

wherein each of $R^1$ and $R^2$ independently is hydrogen, a $C_{1-8}$ alkyl group, a $C_{2-8}$ alkenyl group, a $C_{1-8}$ alkoxy group, a $C_{1-8}$ alkyl group having one to three halogen atoms, a $C_{1-8}$ alkoxy group having one to three halogen atoms, an aralkyl group consisting of a $C_{6-10}$ aryl moiety and a $C_{1-3}$ alkylene moiety, a halogen atom, hydroxyl, nitro, cyano, amino, a $C_{1-8}$ alkylamino group, a $C_{2-8}$ dialkylamino group, a $C_{2-8}$ acylamino group, a $C_{2-8}$ acylamino group having one to three halogen atoms, a $C_{1-8}$ alkylsulfonylamino group, carboxyl, a $C_{2-8}$ acyl group, an alkoxycarbonyl group comprising a $C_{1-8}$ alkoxy moiety, carbamoyl, a $C_{1-8}$ alkylthio group, a $C_{1-8}$ alkylsulfinyl group, a $C_{1-8}$ alkyl-sulfonyl group, or sulfamoyl;

$R^3$ is hydrogen, a $C_{1-8}$ alkyl group, a $C_{2-8}$ alkenyl group, a $C_{1-8}$ alkyl group having one to three halogen atoms, or an aralkyl group consisting of a $C_{6-10}$ aryl moiety and a $C_{1-3}$ alkylene moiety;

$R^4$ is hydrogen, a $C_{1-8}$ alkyl group, a $C_{2-8}$ alkenyl group, a $C_{1-8}$ alkoxy group, a $C_{1-8}$ alkyl group having one to three halogen atoms, a $C_{1-8}$ alkoxy group having one to three halogen atoms, an aralkyl group consisting of a $C_{6-10}$ aryl moiety and a $C_{1-3}$ alkylene moiety, a $C_{1-8}$ alkyl group having hydroxyl, a halogen atom, hydroxyl, nitro, cyano, amino, a $C_{1-8}$ alkylamino group, a $C_{1-5}$ alkylamino group having one to five halogen atoms, a $C_{2-8}$ dialkylamino group, a $C_{2-8}$ acylamino group, a $C_{2-8}$ acylamino group having one to three halogen atoms, a $C_{1-8}$ alkylsulfonylamino group, benzenesulfonylamino optionally having one or more substituents, carboxyl, a $C_{2-8}$ acyl group, an alkoxycarbonyl group comprising a $C_{1-8}$ alkoxy moiety, carbamoyl, a $C_{1-8}$ alkylthio group, a $C_{1-8}$ alkylsulfinyl group, a $C_{1-8}$ alkylsulfonyl group, sulfamoyl, phenyl optionally having one or more substituents, or a heterocyclic group optionally having one or more substituents;

the ring shown below is a five-membered to eight-membered ring optionally comprising one or two nitrogen atoms as the members of the ring, and being condensed with the benzene ring at the positions of 1 and 2 of the benzene ring; and

the ring shown below is an aromatic ring selected from the group consisting of benzene ring, naphthalene ring, pyridine ring, pyrimidine ring, quinoline ring, indole ring, indoline ring, benzimidazole ring, pyrazole ring, indazole ring, benzisoxazole ring, and benzotriazole ring,

provided that $R^4$ is neither hydrogen, a $C_{1-8}$ alkyl group, nor a halogen atom in the case that the ring shown below is benzene ring.

The invention also relates to a compound having the following formula (II) or a pharmacologically acceptable salt thereof:

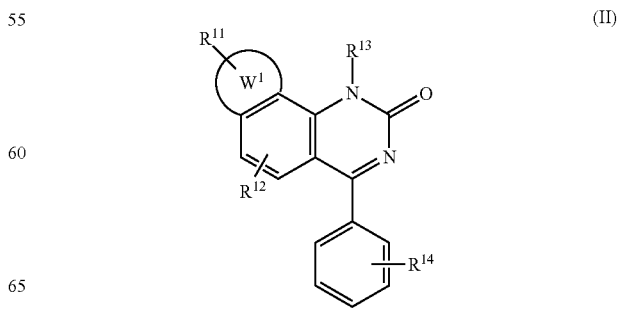

(II)

wherein each of $R^{11}$ and $R^{12}$ independently is hydrogen, a $C_{1-8}$ alkyl group, a $C_{2-8}$ alkenyl group, a $C_{1-8}$ alkoxy group, a $C_{1-8}$ alkyl group having one to three halogen atoms, a $C_{1-8}$ alkoxy group having one to three halogen atoms, an aralkyl group consisting of a $C_{6-10}$ aryl moiety and a $C_{1-3}$ alkylene moiety, a halogen atom, hydroxyl, nitro, cyano, amino, a $C_{1-8}$ alkylamino group, a $C_{2-8}$ dialkylamino group, a $C_{2-8}$ acylamino group, a $C_{2-8}$ acylamino group having one to three halogen atoms, a $C_{1-8}$ alkylsulfonylamino group, carboxyl, a $C_{2-8}$ acyl group, an alkoxycarbonyl group comprising a $C_{1-8}$ alkoxy moiety, carbamoyl, a $C_{1-8}$ alkylthio group, a $C_{1-8}$ alkylsulfinyl group, a $C_{1-8}$ alkylsulfonyl group, or sulfamoyl;

$R^{13}$ is hydrogen, a $C_{1-8}$ alkyl group, a $C_{2-8}$ alkenyl group, a $C_{1-8}$ alkyl group having one to three halogen atoms, or an aralkyl group consisting of a $C_{6-10}$ aryl moiety and a $C_{1-3}$ alkylene moiety;

$R^{14}$ is a $C_{2-8}$ alkenyl group, a $C_{1-8}$ alkoxy group, a $C_{1-8}$ alkyl group having one to three halogen atoms, a $C_{1-8}$ alkoxy group having one to three halogen atoms, an aralkyl group consisting of a $C_{1-8}$ aryl moiety and a $C_{1-3}$ alkylene moiety, a $C_{1-8}$ alkyl group having hydroxyl, hydroxyl, nitro, cyano, amino, a $C_{1-8}$ alkylamino group, a $C_{1-5}$ alkylamino group having one to five halogen atoms, a $C_{2-8}$ dialkylamino group, a $C_{2-8}$ acylamino group, a $C_{2-8}$ acylamino group having one to three halogen atoms, a $C_{1-8}$ alkylsulfonylamino group, benzenesulfonylamino optionally having one or more substituents, carboxyl, a $C_{2-8}$ acyl group, an alkoxycarbonyl group comprising a $C_{1-8}$ alkoxy moiety, carbamoyl, a $C_{1-8}$ alkylthio group, a $C_{1-8}$ alkylsulfinyl group, a $C_{1-8}$ alkylsulfonyl group, sulfamoyl, phenyl optionally having one or more substituents, or a heterocyclic group optionally having one or more substituents; and the ring shown below is naphthalene ring, tetrahydronaphthalene ring, or indan ring.

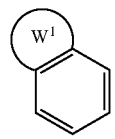

The invention also relates to a $P2X_4$ receptor antagonist containing a compound represented by the formula (I) or (II), or its pharmacologically acceptable salt as an active ingredient.

The invention further relates to a preventive or therapeutic agent for neuropathic pains containing a compound represented by the formula (I) or (II), or its pharmacologically acceptable salt as an active ingredient.

THE EMBODIMENTS OF THE INVENTION

The present invention is described below in more detail.

In the compound of the present invention represented by the formula (I), the alkyl group having 1 to 8 carbon atoms for $R^1$, $R^2$, $R^3$, and $R^4$ can be methyl, ethyl, propyl, isopropyl, butyl, isobutyl, t-butyl, pentyl, or hexyl.

The alkenyl group having 2 to 8 carbon atoms for $R^1$, $R^2$, $R^3$, and $R^4$ can be allyl.

The alkyl group having 1 to 8 carbon atoms substituted with one to three halogen atoms for $R^1$, $R^2$, $R^3$, and $R^4$ can be methyl, ethyl, propyl, isopropyl, butyl, or t-butyl substituted with one to three halogen atoms such as 1 to 3 fluoro, chloro, or bromo atoms, and preferably is trifluoromethyl, chloromethyl, 2-chloroethyl, 2-bromoethyl, or 2-fluoroethyl.

The aralkyl group consisting of an aryl moiety having 6 to 10 carbon atoms and an alkylene moiety having 1 to 3 carbon atoms for $R^1$, $R^2$, $R^3$, and $R^4$ can be benzyl.

The alkoxy group having 1 to 8 carbon atoms for $R^1$, $R^2$, and $R^4$ can be methoxy, ethoxy, propoxy, isopropoxy, butoxy, isobutoxy, t-butoxy, pentyloxy, or hexyloxy.

The alkoxy group having 1 to 8 carbon atoms substituted with one to three halogen atoms for $R^1$, $R^2$, and $R^4$ can be methoxy, ethoxy, propoxy, isopropoxy, butoxy, isobutoxy, or t-butoxy substituted with one to three halogen atoms such as 1 to 3 fluoro, chloro, or bromo atoms, and preferably include trifluoromethoxy, chloromethoxy, 2-chloroethoxy, 2-bromoethoxy, or 2-fluoroethoxy.

The halogen atom for $R^1$, $R^2$, and $R^4$ can be fluoro, chloro, or bromo atom.

The alkylamino group having 1 to 8 carbon atoms for $R^1$, $R^2$, and $R^4$ can be methylamino or ethylamino.

The alkylamino group having 1 to 5 carbon atoms substituted with 1 to 5 halogen atoms for $R^4$ can be 2,2,2-trifluoroethylamino.

The dialkylamino group having 2 to 8 carbon atoms for $R^1$, $R^2$, and $R^4$ can be dimethylamino or diethylamino.

The acylamino group having 2 to 8 carbon atoms for $R^1$, $R^2$, and $R^4$ can be acetylamino.

The acylamino group having 2 to 8 carbon atoms substituted with one to three halogen atoms for $R^1$, $R^2$, and $R^4$ can be trifluoromethylcarbonylamino.

The alkylsulfonylamino group having 1 to 8 carbon atoms for $R^1$, $R^2$, and $R^4$ can be methylsulfonylamino. The acyl group having 2 to 8 carbon atoms for $R^1$, $R^2$, and $R^4$ can be acetyl.

The alkoxycarbonyl group comprising an alkoxy moiety having 1 to 8 carbon atoms for $R^1$, $R^2$, and $R^4$ can be methoxycarbonyl or ethoxycarbonyl.

The alkylthio group having 1 to 8 carbon atoms for $R^1$, $R^2$, and $R^4$ can be methylthio.

The alkylsulfinyl group having 1 to 8 carbon atoms for $R^1$, $R^2$, and $R^4$ can be methylsulfinyl.

The alkylsulfonyl group having 1 to 8 carbon atoms for $R^1$, $R^2$, and $R^4$ can be methylsulfonyl.

The alkyl group having 1 to 8 carbon atoms substituted with hydroxyl for $R^4$ can be hydroxymethyl.

With respect to the benzenesulfonylamino optionally having one or more substituents for $R^4$, the substituent preferably is selected from the group consisting of an alkyl group having 1 to 8 carbon atoms (such as methyl, ethyl), an alkoxy group having 1 to 8 carbon atoms (such as methoxy, ethoxy), a halogen atom (such as fluoro atom, chloro atom), and nitro. It preferably is o-nitrobenzenesulfonylamino.

With respect to the phenyl optionally having one or more substituents for $R^4$, the substituent preferably is an alkyl group having 1 to 8 carbon atoms (such as methyl, ethyl), an alkyl group having 1 to 8 carbon atoms substituted with one to three halogen atoms (such as trifluoromethyl), a halogen atom (such as fluoro atom), or cyano.

The heterocyclic group optionally having one or more substituents for $R^4$ preferably is tetrazolyl, triazolyl, pyridyl, imidazolyl, oxazolyl, or triazolyl.

With respect to the heterocyclic group optionally having one or more substituents for $R^4$, the substituent preferably is an alkyl group having 1 to 8 carbon atoms (such as methyl, ethyl), an alkyl group having 1 to 8 carbon atoms substituted with one to three halogen atoms (such as trifluoromethyl), a halogen atom (such as fluoro atom), cyano, or oxo.

$R^1$, $R^2$, and $R^4$ in the formula (I) can be the same or different two or more substituents attached to the rings to which $R^1$, $R^2$, and $R^4$ are attached.

Examples of $R^{11}$, $R^{12}$, $R^{13}$, and $R^{14}$ in the formula (II) are the same as the examples of the alkyl group having 1 to 8 carbon atoms, the alkenyl group having 2 to 8 carbon atoms, the alkoxy group having 1 to 8 carbon atoms, the alkyl group having 1 to 8 carbon atoms substituted with one to three halogen atoms, the alkoxy group having 1 to 8 carbon atoms substituted with one to three halogen atoms, the aralkyl group consisting of an aryl moiety having 6 to 10 carbon atoms and an alkylene moiety having 1 to 3 carbon atoms, the alkyl group having 1 to 8 carbon atoms substituted with hydroxyl, the halogen atom, the alkylamino group having 1 to 8 carbon atoms, the alkylamino group having 1 to 5 carbon atoms substituted with 1 to 5 halogen atoms, the dialkylamino group having 2 to 8 carbon atoms, the acylamino group having 2 to 8 carbon atoms, the acylamino group having 2 to 8 carbon atoms substituted with 1 to 3 halogen atoms, the alkylsulfonylamino group having 1 to 8 carbon atoms, the benzenesulfonylamino optionally having one or more substituents, the acyl group having 2 to 8 carbon atoms, the alkoxycarbonyl group comprising an alkoxy moiety having 1 to 8 carbon atoms, the alkylthio group having 1 to 8 carbon atoms, the alkylsulfinyl group having 1 to 8 carbon atoms, the alkylsulfonyl group having 1 to 8 carbon atoms, the phenyl optionally having one or more substituents, and the heterocyclic group optionally having one or more substituents for $R^1$, $R^2$, $R^3$, and $R^4$ in the formula (I).

With respect to the heterocyclic group optionally having one or more substituents for $R^{14}$ in the formula (II), examples of the substituents are the same as the examples of the alkyl group having 1 to 8 carbon atoms, the alkoxy group having 1 to 8 carbon atoms, the alkyl group having 1 to 8 carbon atoms substituted with one to three halogen atoms, the alkoxy group having 1 to 8 carbon atoms substituted with one to three halogen atoms, the halogen atoms, the alkylamino group having 1 to 8 carbon atoms, and the dialkylamino group having 2 to 8 carbon atoms for $R^1$ to $R^4$ in the formula (I).

$R^{11}$, $R^{12}$, and $R^{14}$ in the formula (II) can be the same or different two or more substituents attached to the rings to which $R^{11}$, $R^{12}$, and $R^{14}$ are attached.

The compound of the present invention of the formula (I) preferably is the following compound.

(1) A compound having the formula (I) or a pharmacologically acceptable salt thereof, wherein each of $R^1$ and $R^2$ independently is hydrogen, a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, or amino.

(2) A compound having the formula (I), a compound of (1), or a pharmacologically acceptable salt thereof, wherein $R^3$ is hydrogen or a $C_{1-8}$ alkyl group.

(3) A compound having the formula (I), a compound of (1) or (2), or a pharmacologically acceptable salt thereof, wherein $R^4$ is hydrogen, a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, a $C_{1-8}$ alkyl group having hydroxyl, a halogen atom, hydroxyl, cyano, amino, a $C_{1-8}$ alkylamino group, a $C_{2-8}$ dialkylamino group, a $C_{1-8}$ alkylsulfonylamino group, benzenesulfonylamino optionally having one or more substituents, phenyl optionally having one or more substituents, or a heterocyclic group optionally having one or more substituents.

(4) A compound having the formula (I), a compound of (1) or (2), or a pharmacologically acceptable salt thereof, wherein $R^4$ is a heterocyclic group optionally having one or more substituents, said heterocyclic group being tetrazolyl, triazolyl, pyridyl, imidazolyl, oxazolyl, or thiazolyl, and said substituents being selected from the group consisting of a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, amino, a $C_{1-8}$ alkylamino group, and a $C_{2-8}$ dialkylamino group.

(5) A compound having the formula (I), a compound of (1) or (2), or a pharmacologically acceptable salt thereof, wherein $R^4$ is a $C_{1-8}$ alkoxy group, a $C_{1-8}$ alkyl group having one to three halogen atoms, a $C_{1-8}$ alkoxy group having one to three halogen atoms, hydroxyl, cyano, amino, a $C_{1-8}$ alkylamino group, a $C_{2-8}$ dialkylamino group, or benzenesulfonylamino optionally having one or more substituents, said substituents being selected from the group consisting of a $C_{1-8}$ alkyl group, a $C_{1-8}$ alkoxy group, a halogen atom, and nitro.

(6) A compound having the formula (I), a compound of one of (1) to (5), or a pharmacologically acceptable salt thereof, wherein the ring shown below is naphthalene ring, tetrahydronaphthalene ring, or indan ring.

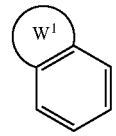

(7) A compound having the formula (I), a compound of one of (1) to (6), or a pharmacologically acceptable salt thereof, wherein the ring shown below is benzene ring or indole ring.

The compound of the present invention of the formula (II) preferably is the following compound.

(8) A compound having the formula (II) or a pharmacologically acceptable salt thereof, wherein each of $R^{11}$ and $R^{12}$ independently is hydrogen, a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, or amino.

(9) A compound having the formula (II), a compound of (8), or a pharmacologically acceptable salt thereof, wherein $R^{13}$ is hydrogen.

(10) A compound having the formula (II), a compound of (8) or (9), or a pharmacologically acceptable salt thereof, wherein $R^{14}$ is a $C_{1-8}$ alkoxy group, a $C_{1-8}$ alkyl group having one to three halogen atoms, a $C_{1-8}$ alkoxy group having one to three halogen atoms, a $C_{1-8}$ alkyl group having hydroxyl, hydroxyl, cyano, amino, a $C_{1-8}$ alkylamino group, a $C_{2-8}$ dialkylamino group, a $C_{1-8}$ alkylsulfonylamino group, benzenesulfonylamino optionally having one or more substituents, phenyl optionally having one or more substituents, or a heterocyclic group optionally having one or more substituents.

(11) A compound having the formula (II), a compound of (8) or (9), or a pharmacologically acceptable salt thereof, wherein $R^{14}$ is a heterocyclic group optionally having one or more substituents, said heterocyclic group being tetrazolyl, triazolyl, pyridyl, imidazolyl, oxazolyl, or triazolyl, and said substituents being selected from the group consisting of a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, amino, a $C_{1-8}$ alkylamino group, and a $C_{2-8}$ dialkylamino group.

(12) A compound having the formula (II), a compound of (8) or (9), or a pharmacologically acceptable salt thereof, wherein $R^{14}$ is a $C_{1-8}$ alkoxy group, a $C_{1-8}$ alkyl group having one to three halogen atoms, a $C_{1-8}$ alkoxy group having one to three halogen atoms, hydroxyl, cyano, amino, a $C_{1-8}$ alkylamino group, a $C_{2-8}$ dialkylamino group, or benzenesulfonylamino optionally having one or more substituents, said substituents being selected from the group consisting of a $C_{1-8}$ alkyl group, a $C_{1-8}$ alkoxy group, a halogen atom, and nitro.

(13) A compound having the formula (II), a compound of (1) or (2), or a pharmacologically acceptable salt thereof, wherein the ring shown below is naphthalene ring.

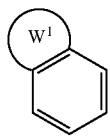

The pharmacologically acceptable salts of the compound represented by the formula (I) or (II) include a hydrochloride salt and an alkali metal (e.g., sodium, potassium, lithium) salt.

The compound of the present invention can be a geometrical isomer or an optical isomer such as an optically active substance and racemic modification, each of which is included within the scope of the invention.

The schemes for synthesis of the compound of the invention represented by the formula (I) are shown below.
[Synthesis Method 1]

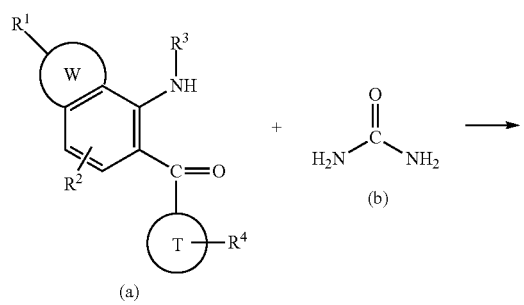

In the above-illustrated formula, $R^1$, $R^2$, $R^3$, $R^4$, and the following rings are defined above.

The compound of the invention represented by the formula (c) can be obtained by subjecting the compound represented by the formula (a) and urea represented by the formula (b) to a ring-closing reaction in the presence of a solvent such as acetic acid.

The compound represented by the formula (a) can be synthesized, for example by the following process.

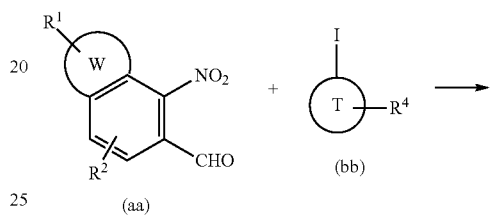

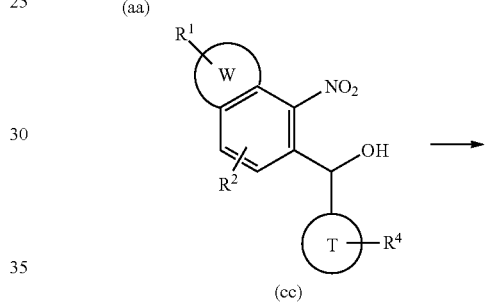

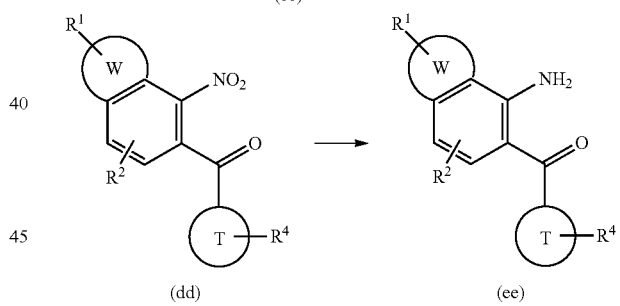

In the above-illustrated formula, $R^1$, $R^2$, $R^4$, and the following rings are defined above.

The compound represented by the formula (cc) can be obtained by subjecting the compound represented by the formula (aa) and the compound represented by the formula (bb) to a reaction in the presence of bis(2-dimethylaminoethyl) ether, isopropylmagnesium chloride in a solvent such as THF. The compound represented by the formula (dd) can be obtained by oxidizing hydroxyl of the compound represented by the formula (cc) to carbonyl in the presence of an oxidizing agent such as pyridinium dichromate in a solvent such as dichloromethane. The compound represented by the formula (ee) can be obtained by reducing nitro of the compound represented by the formula (dd) to amino in the presence of a reducing agent such as iron powder in a solvent such as acetic acid, methanol.

[Synthesis Method 2]

$R^4$ is tetrazolyl in the formula (I).

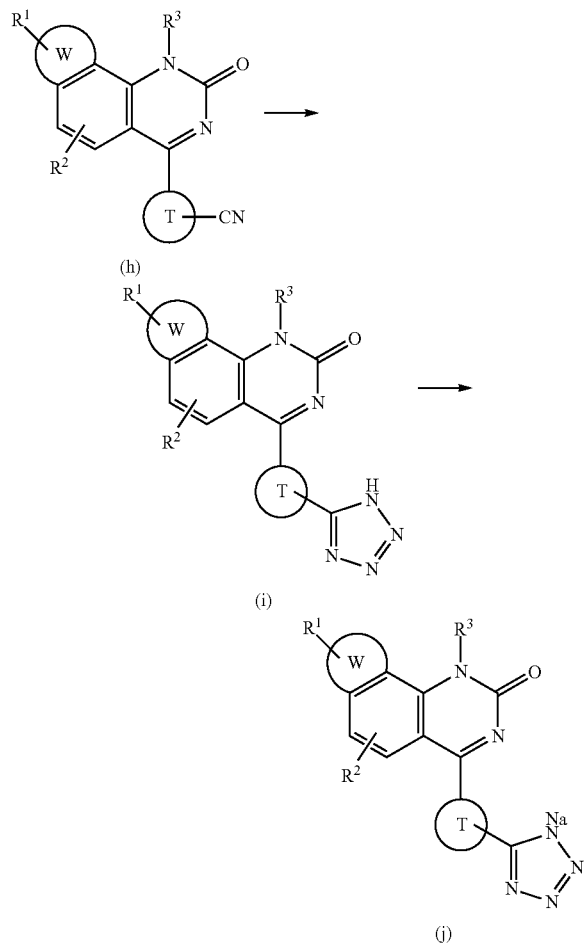

In the above-illustrated formula, $R^1$, $R^2$, $R^3$, and the following rings are defined above.

The tetrazole compound represented by the formula (i) can be obtained by reaction of the nitrile compound represented by the formula (h) with an azide compound such as tri-n-butyltin azide, sodium azide, in the presence of a solvent such as toluene, DMF.

The metal salt represented by the formula (j) can be obtained by reaction of the tetrazole compound represented by the formula (i) with an inorganic base such as sodium hydrogencarbonate, potassium hydrogencarbonate in the presence of a solvent such as water, ethanol.

The other compounds of the present invention represented by the formulas (I) and (II) can also be prepared by referring to the above-mentioned synthesis methods, the below described Examples, the patent documents described above, and the other known documents.

Examples of the obtained representative compounds of the present invention are shown below.

(Representative Compound 1)

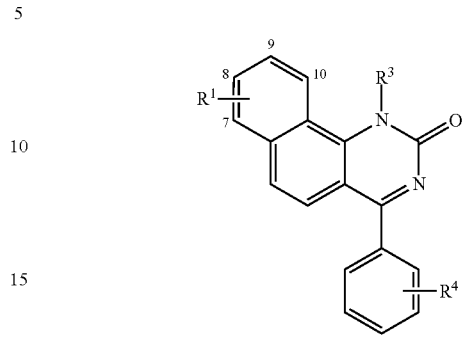

In the above-illustrated formula, $R^1$, $R^3$, and $R^4$ are shown in Table 1.

TABLE 1

| $R^1$ | $R^3$ | $R^4$ |
|---|---|---|
| H | H | 3-OH |
| 8-CH$_3$ | H | 3-OCH$_3$ |
| 8-Cl | H | 4-OH |
| 9-CH$_3$ | H | 3,4-OH |
| 9-Cl | H | 3-CN |
| H | H | 4-CN |
| H | H | 3-CO$_2$H |
| H | H | 3-NH$_2$ |
| H | H | 3-NHCH$_3$ |
| H | CH$_3$ | 3-NHCH$_3$ |
| H | C$_2$H$_5$ | 3-NHC$_2$H$_5$ |
| H | H | 3-NHCH$_2$CF$_3$ |
| H | H | 3-NHSO$_2$-phenyl |
| H | H | 3-NHSO$_2$-(2-NO$_2$)phenyl |
| H | H | 1H-tetrazol-5-yl |
| H | H | 1H-tetrazol-1-yl |

(Representative Compound 2)

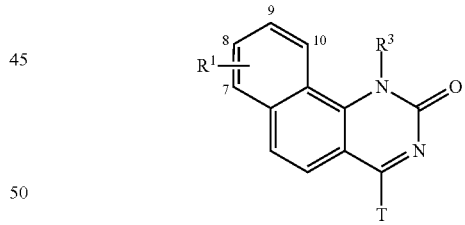

In the above-illustrated formula, $R^1$, $R^3$, and T are shown in Table 2.

TABLE 2

| $R^1$ | $R^3$ | T |
|---|---|---|
| H | H | 1H-indol-6-yl |
| 8-CH$_3$ | H | 1H-indol-4-yl |
| 8-Cl | H | 1H-indazol-6-yl |
| 9-CH$_3$ | H | 1H-indazol-4-yl |
| 9-Cl | H | 1H-indolin-6-yl |
| H | CH$_3$ | 1H-benzimidazol-6-yl |
| H | C$_2$H$_5$ | 1H-benzotriazol-6-yl |
| H | H | 3-methylbenzisoxazol-6-yl |
| H | H | pyridin-3-yl |

TABLE 2-continued

| R¹ | R³ | T |
|---|---|---|
| H | H | 1H-pyrazol-4-yl |
| H | H | pyridin-2-yl |
| H | H | 4-methylpyridin-2-yl |
| H | H | 2-bromopyridin-5-yl |

(Representative Compound 3)

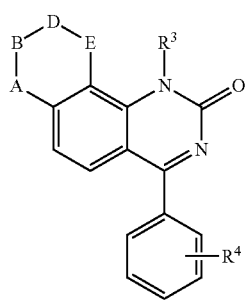

In the above-illustrated formula, A-B-D-E, $R^3$, and $R^4$ are shown in Table 3.

TABLE 3

| A—B—D—E | R³ | R⁴ |
|---|---|---|
| CH₂—CH₂—CH₂—CH₂ | H | 3-OH |
| CH₂—CH₂—CH₂ | H | 3-OCH₃ |
| CH₂—CH₂—CH₂—CH₂—CH₂ | H | 4-OH |
| CH₂—CH₂—CH₂—CH₂—CH₂—CH₂ | H | 3,4-OH |
| CH₂—CH₂—CH₂—CH₂ | H | 3-CN |
| CH₂—CH₂—NH—CH₂ | H | 4-CN |
| CH₂—CH₂—CH₂—CH₂ | H | 3-CO₂H |
| CH₂—CH₂—NH—CH₂ | H | 3-NH₂ |
| CH₂—CH₂—CH₂—CH₂ | H | 3-NHCH₃ |
| CH₂—CH₂—CH₂—CH₂ | CH₃ | 3-NHCH₃ |
| CH₂—CH₂—CH₂—CH₂ | C₂H₅ | 3-NHC₂H₅ |
| CH₂—CH₂—CH₂—CH₂ | H | 3-NHCH₂CF₃ |
| CH₂—CH₂—CH₂—CH₂ | H | 3-NHSO₂-phenyl |
| CH₂—CH₂—CH₂—CH₂ | H | 3-NHSO₂-(2-NO₂)phenyl |
| CH₂—CH₂—CH₂—CH₂ | H | 1H-tetrazol-5-yl |
| CH₂—NH—CH₂—CH₂ | H | 1H-tetrazol-1-yl |

(Representative Compound 4)

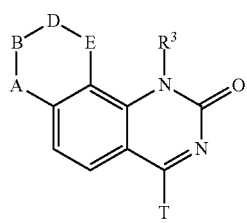

In the above-illustrated formula, A-B-D-E, $R^3$, and T are shown in Table 4.

TABLE 4

| A—B—D—E | R³ | T |
|---|---|---|
| CH₂—CH₂—CH₂—CH₂ | H | 1H-indol-6-yl |
| CH₂—CH₂—CH₂ | H | 1H-indol-4-yl |
| CH₂—CH₂—CH₂—CH₂—CH₂ | H | 1H-indazol-6-yl |

TABLE 4-continued

| A—B—D—E | R³ | T |
|---|---|---|
| CH₂—CH₂—CH₂—CH₂—CH₂—CH₂ | H | 1H-indazol-4-yl |
| CH₂—CH₂—CH₂—CH₂ | CH | 1H-indolin-6-yl |
| CH₂—NH—CH₂—CH₂ | C₂H₅ | 1H-benzimidazol-6-yl |
| CH₂—CH₂—CH₂—CH₂ | H | 1H-benzotriazol-6-yl |
| CH₂—CH₂—CH₂—CH₂ | H | 3-methylbenzisoxazol-6-yl |
| CH₂—CH₂—CH₂—CH₂ | H | pyridin-3-yl |
| CH₂—N(CH₃)—CH₂—CH₂ | H | 1H-pyrazol-4-yl |
| CH₂—CH(CH₃)—CH₂—CH₂ | H | pyridin-2-yl |
| CH₂—CH₂—CH(CH₃)—CH₂ | H | 4-methylpyridin-2-yl |
| CH₂—CH₂—CH(CH₃)—CH₂ | H | 2-bromopyridin-5-yl |

The pharmacological effects of the present invention are described below.

$P2X_4$ antagonism of the compound of the present invention is measured as described below.

1321N1 cells stably expressing human $P2X_4$ receptors were plated in 96-well assay plate and cultured 24 hours at 37° C. in an atmosphere of 5% $CO_2$ for intracellular calcium assay. Fura-2 AM calcium fluorescent indicator was used for the intracellular calcium assay. Fura-2 AM was dissolved in an assay buffer, and the solution was loaded onto cells. The obtained plate was used for fluorescent assay. Test compounds were treated to cells 15 minutes before the addition of ATP, and the response to intracellular calcium influx induced by addition of ATP was monitored by a micro plate reader. The fluorescence ratio of excitations wavelengths of 340 nm and 380 nm was used as the index of intracellular calcium change. The inhibition activities of the test compounds were calculated by comparison with the absence of the test compound (control).

As is evident from the below-described results shown in Example 9, the compound of the present invention shows excellent $P2X_4$ receptor antagonism.

Therefore, it is considered that the diazepine derivative represented by the formula (I), (II), or its pharmacologically acceptable salt, which shows $P2X_4$ receptor antagonism, is effective as an agent for prevention or treatment of nociceptive, inflammatory, and neuropathic pains. In more detail, it is effective as a preventive or therapeutic agent for pains caused by various cancers, diabetic neuritis, viral diseases such as herpes, and osteoarthritis. The preventive or therapeutic agent of the present invention can also be used in combination with other agents such as opioid analgesic (e.g., morphine, fentanyl), sodium channel inhibitor (e.g., novocaine, lidocaine), or NSAIDs (e.g., aspirin, ibuprofen). The agent for pains caused by cancers can be used in combination with a carcinostatic such as a chemotherapic.

The compound of the present invention can be administered to human beings by ordinary administration methods such as oral administration or parenteral administration.

The compound can be granulated in ordinary manners for the preparation of pharmaceuticals. For instance, the compound can be processed to give pellets, granule, powder, capsule, suspension, injection, suppository, and the like.

Ordinary additives such as vehicles, disintegrators, binders, lubricants, dyes, and diluents are used for the preparation of these pharmaceuticals. As the vehicles, lactose, D-mannitol, crystalline cellulose, and glucose can be mentioned. Further, there can be mentioned starch and carboxymethylcellulose calcium (CMC-Ca) as the disintegrators, magnesium stearate and talc as the lubricants, and hydroxypropylcellulose (HPC), gelatin and polyvinylpirrolidone (PVP) as the binders. The preparation of an injection can be made using solvents, stabilizers, dissolution-aids, suspensions, emulsifiers, soothing agents, buffers, or preservatives.

The compound of the invention can be administered to an adult generally in an amount of approx. 0.01 mg to 100 mg a day by parenteral administration and 1 mg to 2,000 mg a day by oral administration. The dosage can be adjusted in consideration of age and conditions of the patient.

The present invention is further described by the following non-limiting examples.

EXAMPLES

Example 1

4-(3-Cyanophenyl)-1H-benzo[h]quinazolin-2-one (1) 3-[Hydroxy(1-nitronaphthalen-2-yl)methyl]benzonitrile To a solution of bis(2-dimethylaminoethyl)ether (5.62 mL, 29.8 mmol) in THF (125 mL) was added a solution of 2M isopropylmagnesium chloride in THF (14.9 mL, 29.8 mmol) dropwise under $N_2$ atmosphere at room temperature, and stirred for 20 min. To the mixture was added 3-iodobenzonitrile (5.69 g, 24.9 mmol), and stirred for 30 min. To an ice-cold solution of the resultant mixture was added 1-nitro-2-naphthaldehyde, and stirred at room temperature for 1 hour. To the reaction mixture was poured 1M hydrochloric acid, and extracted with ethyl acetate. The organic layer was washed with water, dried over anhydrous sodium sulfate. The solvent was removed under reduced pressure. The residue was purified by silica gel column chromatography (hexane/ethyl acetate=4/1), to give the titled compound as a green orange oil (7.37 g, yield 97%).

$^1$H-NMR (CDCl$_3$, 400 MHz) δ: 2.75 (1H, d, J=4 Hz), 6.12 (1H, d, J=4 Hz), 7.4-7.5 (2H, m), 7.59 (1H, d, J=8 Hz), 7.6-7.7 (3H, m), 7.7-7.8 (2H, m), 7.92 (1H, d, J=9 Hz), 8.02 (1H, d, J=12 Hz).

(2) 3-(1-Nitro-2-naphthoyl)benzonitrile

To a solution of 3-[hydroxy(1-nitronaphthalen-2-yl)methyl]benzonitrile (7.37 g, 24.2 mmol) in dichloromethane (70 mL) was added silica gel (30 g) and pyridinium dichromate (13.7 g, 36.3 mmol), and stirred for 18 hours. The reaction mixture was filtered, and the residue was washed with chloroform. The filtrate was concentrated to dryness, and the residue was recrystallized from ethyl acetate, and washed with hexane to give the titled compound as a pale yellow crystal (6.32 g, yield 86%).

$^1$H-NMR (CDCl$_3$, 400 MHz) δ: 7.52 (1H, d, J=8 Hz), 7.64 (1H, t, J=8 Hz), 7.7-7.9 (2H, m), 7.90 (1H, dt, J=1 Hz, 7 Hz), 8.0-8.1 (3H, m), 8.1-8.3 (2H, m).

(3) 3-(1-Amino-2-naphthoyl)benzonitrile 3-(1-nitro-2-naphthoyl)benzonitrile (6.22 g, 20.6 mmol) was dissolved at 65° C. in acetic acid (150 mL), ethanol (150 mL) and water (15 mL). After cooled to room temperature, to the solution was added iron powder (6.67 g, 119 mmol). To the mixture was stirred at 65° C. for 1 hour, and cooled to room temperature. The resultant mixture was added silica gel (100 g), filtered, and the residue was washed with ethyl acetate. The filtrate and washings were combined, washed with a saturated aqueous sodium bicarbonate solution and saturated brine. The organic layer was dried over anhydrous sodium sulfate. The solvent was removed under reduced pressure, and the residue was purified by silica gel column chromatography (chloroform), to give the titled compound as a yellow crystal (5.40 g, yield 96%).

$^1$H-NMR (CDCl$_3$, 400 MHz) δ: 7.00 (1H, d, J=9 Hz), 7.30 (1H, d, J=9 Hz), 7.5-7.7 (5H, m), 7.76 (1H, d, J=7 Hz), 7.80 (1H, dt, J=1 Hz, 9 Hz), 7.8-7.9 (1H, m), 7.9-8.0 (1H, m), 7.98 (1H, d, J=8 Hz).

(4) 4-(3-Cyanophenyl)-1H-benzo[h]quinazolin-2-one

To a solution of 3-(1-amino-2-naphthoyl)benzonitrile (200 mg, 0.734 mmol) in acetic acid (2 mL) was added urea (132 mg, 2.20 mmol). The mixture was heated under reflux for 18 hours. The reaction mixture was cooled to room temperature, and filtered. The obtained crystal was washed with ethyl acetate, and dried to give the titled compound as a yellow crystal (130 mg, yield 60%).

$^1$H-NMR (DMSO-d$_6$, 400 MHz) δ: 7.5-7.8 (3H, m), 7.8-7.9 (2H, m), 8.04 (2H, d, J=8 Hz), 8.09 (1H, d, J=8 Hz), 8.16 (1H, s), 8.58 (1H, d, J=8 Hz), 12.47 (1H, br s).

FAB-MS (m/z): 298 (M+1).

Example 2

4-[3-(1H-Tetrazol-5-yl)phenyl]-1H-benzo[h]quinazolin-2-one sodium salt (1) 4-[3-(1H-Tetrazol-5-yl)phenyl]-1H-benzo[h]quinazolin-2-one To a solution of 4-(3-cyanophenyl)-1H-benzo[h]quinazolin-2-one (112 mg, 0.377 mmol) in DMF (2 mL) was added tri-n-butyltin azide (312 μL, 1.13 mmol), and stirred at 110° C. for 18 hours. After cooled to room temperature, the reaction mixture was poured into 1M sodium hydroxide, and washed with ethyl acetate. After aqueous layer was neutralized with 1M hydrochloric acid, the precipitated solid was collected by filtration, washed with methanol, and with water. The obtained crystal was dried to give the titled compound as a yellow crystal (70 mg, yield 55%).

$^1$H-NMR (DMSO-d$_6$, 400 MHz) δ: 7.6-8.1 (7H, m), 8.29 (1H, d, J=7 Hz), 8.38 (1H, s), 9.02 (1H, d, J=7 Hz), 12.47 (1H, br s).

(2) 4-[3-(1H-Tetrazol-5-yl)phenyl]-1H-benzo[h]quinazolin-2-one sodium salt

To a suspension of 4-[3-(1H-tetrazol-5-yl)phenyl]-1H-benzo[h]quinazolin-2-one (65 mg, 0.191 mmol) in ethanol (5 mL) and water (2 mL) was added sodium bicarbonate (3.5 mg, 0.042 mmol). After dissolved by heating, the mixture was stirred at room temperature for 30 min. After filtration, the filtrate was concentrated under reduced pressure, to give the titled compound as a yellow powder (58 mg, yield 84%).

$^1$H-NMR (DMSO-d$_6$, 400 MHz) δ: 7.5-7.7 (4H, m), 7.71 (1H, t, J=8 Hz), 7.79 (1H, d, J=8 Hz), 7.99 (1H, d, J=8 Hz), 8.20 (1H, d, J=7 Hz), 8.30 (1H, s), 9.01 (1H, d, J=8 Hz), 12.32 (1H, br s).

FAB-MS (m/z): 363 (M+1).

Example 3

4-(3-Methoxyphenyl)-1H-benzo[h]quinazolin-2-one

To a solution of 1-amino-2-(3-methoxybenzoil)naphthalene (195 mg, 0.702 mmol) in acetic acid (2 mL) was added urea (126 mg, 2.11 mmol). The mixture was heated under reflux for 18 hours. The reaction mixture was cooled to room temperature, and filtered. The obtained crystal was washed with ethyl acetate, and dried to give the titled compound as a yellow crystal (151 mg, yield 71%).

$^1$H-NMR (DMSO-d$_6$, 400 MHz) δ: 3.84 (3H, s), 7.1-7.3 (3H, m), 7.51 (1H, t, J=8 Hz), 7.5-7.7 (2H, m), 7.72 (1H, t, J=8 Hz), 7.80 (1H, t, J=7 Hz), 8.01 (1H, d, J=8 Hz), 8.99 (1H, d, J=8 Hz), 12.35 (1H, br s).

FAB-MS (m/z): 303 (M+1).

Example 4

4-(3-Hydroxyphenyl)-1H-benzo[h]quinazolin-2-one sodium salt (1)

4-(3-Hydroxyphenyl)-1H-benzo[h]quinazolin-2-one

To an ice-cold suspension of 4-(3-methoxyphenyl)-1H-benzo[h]quinazolin-2-one (120 mg, 0.397 mmol) in dichloromethane (2 mL) was added 1M boron tribromide in dichloromethane (400 μL, 0.400 mmol). The mixture was stirred at room temperature for 18 hours. The resultant mixture was poured into a saturated aqueous sodium bicarbonate solution. The precipitated solid was collected by filtration, purified by silica gel column chromatography (chloroform/methanol=97/3), and recrystallized from DMF/methanol to give the titled compound as a yellow crystal (41 mg, yield 36%).

$^1$H-NMR (DMSO-d$_6$, 400 MHz) δ: 6.99 (1H, dd, J=1 Hz, 8 Hz), 7.0-7.1 (2H, m), 7.39 (1H, t, J=8 Hz), 7.61 (1H, d, J=10 Hz), 7.64 (1H, d, J=10 Hz), 7.72 (1H, t, J=8 Hz), 7.80 (1H, t, J=7 Hz), 8.00 (1H, d, J=8 Hz), 8.98 (1H, d, J=7 Hz), 9.80 (1H, br s).

(2)

4-(3-Hydroxyphenyl)-1H-benzo[h]quinazolin-2-one sodium salt

To a suspension of 4-(3-hydroxyphenyl)-1H-benzo[h]quinazolin-2-one (30 mg, 0.104 mmol) in THF (4 mL), DMF (1 mL) and water (150 μL) was added a solution of 1M sodium hydroxide (104 μL, 0.104 mmol). The mixture was stirred at 80° C. for 30 min. After the hot mixture was filtered, the filtrate was concentrated under reduced pressure, to give the titled compound as a yellow crystal (33 mg, yield 99%).

$^1$H-NMR (DMSO-d$_6$, 400 MHz) δ: 6.8-6.9 (1H, m), 6.93 (1H, d, J=7 Hz), 7.0-7.1 (2H, m), 7.25 (1H, t, J=8 Hz), 7.40 (1H, d, J=9 Hz), 7.46 (1H, t, J=7 Hz), 7.54 (1H, t, J=7 Hz), 7.69 (1H, d, J=8 Hz), 8.93 (1H, d, J=8 Hz).

FAB-MS (m/z): 311 (M+1).

Example 5

4-(4-Methoxyphenyl)-1H-benzo[h]quinazolin-2-one (1)

(4-methoxyphenyl)(1-nitronaphthalen-2-yl)methanol

The titled compound was prepared from 1-nitro-2-naphthaldehyde and 4-iodoanisole in a procedure similar to that of example 1 (1).

$^1$H-NMR (CDCl$_3$, 400 MHz) δ: 2.53 (1H, d, J=4 Hz), 3.79 (3H, s), 6.09 (1H, d, J=4 Hz), 6.88 (2H, d, J=9 Hz), 7.34 (2H, d, J=8 Hz), 7.5-8.2 (6H, m).

(2)

(4-Methoxyphenyl)(1-nitronaphthalen-2-yl)methanone

The titled compound was prepared from (4-methoxyphenyl)(1-nitronaphthalen-2-yl)methanol in a procedure similar to that of example 1 (2).

$^1$H-NMR (CDCl$_3$, 400 MHz) δ: 3.88 (3H, s), 6.9-7.0 (2H, m), 7.55 (1H, d, J=8 Hz), 7.6-7.8 (2H, m), 7.8-7.9 (2H, m), 8.00 (1H, dd, J=2 Hz, 8 Hz), 8.11 (2H, t, J=9 Hz).

(3) (1-Aminonaphthalene-2-yl)(4-methoxyphenyl)methanone

The titled compound was prepared from (4-methoxyphenyl)(1-nitronaphthalen-2-yl)methanone in a procedure similar to that of example 1 (3).

$^1$H-NMR (CDCl$_3$, 400 MHz) δ: 3.89 (3H, s), 6.9-7.0 (2H, m), 7.02 (1H, d, J=9 Hz), 7.25 (2H, br s), 7.5-7.6 (2H, m), 7.58 (1H, dt, J=8 Hz), 7.6-7.7 (2H, m), 7.75 (1H, d, J=8 Hz), 7.96 (1H, d, J=8 Hz).

(4)

4-(4-methoxyphenyl)-1H-benzo[h]quinazolin-2-one

The titled compound was prepared from (1-aminonaphthalene-2-yl)(4-methoxyphenyl)methanone in a procedure similar to that of example 1 (4).

$^1$H-NMR (DMSO-d$_6$, 400 MHz) δ: 3.87 (3H, s), 7.15 (2H, d, J=9 Hz), 7.6-7.9 (6H, m), 8.01 (1H, d, J=8 Hz), 8.98 (1H, d, J=8 Hz), 12.25 (1H, br s).

Example 6

4-(4-Hydroxyphenyl)-1H-benzo[h]quinazolin-2-one sodium salt (1)

4-(4-Hydroxyphenyl)-1H-benzo[h]quinazolin-2-one

The titled compound was prepared from 4-(4-methoxyphenyl)-1H-benzo[h]quinazolin-2-one in a procedure similar to that of example 4 (1).

$^1$H-NMR (DMSO-d$_6$, 400 MHz) δ: 6.97 (2H, d, J=8 Hz), 7.5-7.9 (6H, m), 8.00 (1H, d, J=7H), 8.97 (1H, s), 10.08 (1H, br s), 12.23 (1H, br s).

(2)

4-(4-Hydroxyphenyl)-1H-benzo[h]quinazolin-2-one sodium salt

The titled compound was prepared from 4-(4-hydroxyphenyl)-1H-benzo[h]quinazolin-2-one in a procedure similar to that of example 4 (2).

$^1$H-NMR (DMSO-d$_6$, 400 MHz) δ: 6.93 (2H, d, J=8 Hz), 7.31 (1H, d, J=9 Hz), 7.5-7.7 (5H, m), 7.84 (1H, d, J=7 Hz), 8.95 (1H, d, J=8 Hz).

Example 7

4-(3-Aminophenyl)-1H-benzo[h]quinazolin-2-one hydrochloride (1)

(3-Bromophenyl)(1-nitronaphthalen-2-yl)methanol

The titled compound was prepared from 1-nitro-2-naphthaldehyde and 1-bromo-3-iodobenzene in a procedure similar to that of example 1 (1).

$^1$H-NMR (CDCl$_3$, 400 MHz) δ: 2.65 (1H, d, J=4 Hz), 6.07 (1H, d, J=4 Hz), 7.21 (1H, t, J=8 Hz), 7.33 (1H, d, J=8 Hz), 7.43 (1H, d, J=8 Hz), 7.51 (1H, d, J=9 Hz), 7.6-7.7 (3H, m), 7.78 (1H, d, J=9 Hz), 7.90 (1H, d, J=7 Hz), 7.96 (1H, d, J=9 Hz).

(2)
(3-Bromophenyl)(1-nitronaphthalen-2-yl)methanone

The titled compound was prepared from (3-bromophenyl)(1-nitronaphthalen-2-yl)methanol in a procedure similar to that of example 1 (2).

$^1$H-NMR (CDCl$_3$, 400 MHz) δ: 7.36 (1H, t, J=8 Hz), 7.53 (1H, d, J=8 Hz), 7.7-7.8 (4H, m), 7.97 (1H, t, J=2 Hz), 8.02 (1H, d, J=9 Hz), 8.15 (1H, d, J=9 Hz), 8.18 (1H, d, J=9 Hz).

(3)
(1-Aminonaphthalene-2-yl)(3-bromophenyl)methanone

The titled compound was prepared from (3-bromophenyl)(1-nitronaphthalen-2-yl)methanone in a procedure similar to that of example 1 (3).

$^1$H-NMR (CDCl$_3$, 400 MHz) δ: 6.99 (1H, d, J=9 Hz), 7.34 (1H, t, J=8 Hz), 7.40 (1H, d, J=9 Hz), 7.4-7.7 (6H, m), 7.75 (1H, d, J=8 Hz), 7.77 (1H, t, J=2 Hz), 7.97 (1H, d, J=9 Hz).

(4)
4-(3-Bromophenyl)-1H-benzo[h]quinazolin-2-one

The titled compound was prepared from (1-aminonaphthalene-2-yl)(3-bromophenyl)methanone in a procedure similar to that of example 1 (4).

$^1$H-NMR (DMSO-d$_6$, 400 MHz) δ: 7.5-7.6 (2H, m), 7.65 (1H, d, J=9 Hz), 7.7-7.9 (4H, m), 7.88 (1H, s), 8.02 (1H, d, J=8 Hz), 8.99 (1H, d, J=8 Hz), 12.43 (1H, br s).

(5)
4-(3-Aminophenyl)-1H-benzo[h]quinazolin-2-one

The mixture of 4-(3-bromophenyl)-1H-benzo[h]quinazolin-2-one (950 mg, 2.71 mmol), 1,4-dioxane (95 mg, 1.08 mmol), sodium tert-butoxide (650 mg, 6.76 mmol), benzophenone imine (681 μL, 4.06 mmol), and (±)-2,2'-bis(diphenylphosphino)-1,1'-binaphthyl (101 mg, 0.16 mmol) was heated under reflux for 16 hours under N$_2$ atmosphere. The solvent was removed under reduced pressure. To the residue was added methanol (50 mL) and 2M hydrochloride (50 mL), and stirred at room temperature for 16 hours. The reaction mixture was filtered to give the titled compound as a yellow solid (191 mg, yield 25%).

$^1$H-NMR (DMSO-d$_6$, 400 MHz) δ: 5.37 (2H, br s), 6.77 (2H, d, J=8 Hz), 6.87 (1H, s), 7.22 (1H, t, J=8 Hz), 7.6-7.8 (3H, m), 7.79 (1H, t, J=8 Hz), 8.00 (1H, d, J=8 Hz), 8.97 (1H, d, J=8 Hz), 12.30 (1H, br s).

(6)
4-(3-Aminophenyl)-1H-benzo[h]quinazolin-2-one hydrochloride

To a solution of 4-(3-aminophenyl)-1H-benzo[h]quinazolin-2-one (25 mg, 0.087 mmol) in chloroform (2 mL)/methanol (1 mL) was added a solution of 4M hydrogen chloride in ethyl acetate (1 mL), and stirred for 1 hour. The solvent was removed under reduced pressure to give the titled compound as a orange powder (30 mg, yield 100%).

$^1$H-NMR (DMSO-d$_6$, 400 MHz) δ: 7.4-7.7 (5H, m), 7.67 (1H, d, J=9 Hz), 7.75 (1H, t, J=8 Hz), 7.83 (1H, t, J=7 Hz), 8.04 (1H, d, J=8 Hz), 9.01 (1H, d, J=9 Hz).

Example 8

N-[3-(2-Oxo-1,2-dihydrobenzo[h]quinazolin-4-yl)phenyl]benzenesulfonamide

To a solution of 4-(3-aminophenyl)-1H-benzo[h]quinazolin-2-one (20 mg, 0.07 mmol) in pyridine (3 mL) was added benzenesulfonyl chloride (127 μL, 0.99 mmol), and stirred at 80° C. for 5 hours. After the solution was cooled to room temperature, the solvent was removed under reduced pressure. The residue was diluted with chloroform, washed with a saturated aqueous sodium bicarbonate solution and dried over anhydrous sodium sulfate. The solvent was removed under reduced pressure, the residue was purified by silica gel column chromatography (hexane/ethyl acetate=4/1), to give the titled compound as a yellow amorphous form (5 mg, yield 15%).

$^1$H-NMR (DMSO-d$_6$, 400 MHz) δ: 7.2-7.4 (4H, m), 7.46 (1H, t, J=8 Hz), 7.5-7.9 (8H, m), 8.04 (1H, d, J=8 Hz), 8.98 (1H, d, J=8 Hz), 10.55 (1H, br s), 12.38 (1H, br s).

Example 9

Experimental Procedure

P2X$_4$ receptor antagonism of the compound of the present invention was measured as described below.

1321N1 cells stably expressing human P2X$_4$ receptors were plated in 96-well assay plate and cultured 24 hours at 37° C. in an atmosphere of 5% CO$_2$ for intracellular calcium assay. Fura-2 AM calcium fluorescent indicator was used for the intracellular calcium assay. Fura-2 AM was dissolved in an assay buffer, and the solution was loaded onto cells. The obtained plate was used for fluorescent assay.

Test compounds were treated to cells 15 minutes before the addition of ATP, and the response to intracellular calcium influx induced by addition of ATP was monitored by a micro plate reader. The fluorescence ratio of excitations wavelengths of 340 nm and 380 nm was used as the index of intracellular calcium change. The inhibition activities of the test compounds were calculated by comparison with the absence of the test compound (control).

Experimental Results

TABLE 9

| Test compound | Inhibition activities (IC$_{50}$ μM) |
| --- | --- |
| Example 2 | 0.16 |

As is evident from Table 9, the compound of the present invention described in Example 2 has excellent P2X$_4$ receptor antagonism.

The invention claimed is:
1. A compound having the following formula (I) or a pharmacologically acceptable salt thereof:

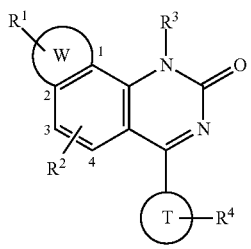

(I)

wherein each of $R^1$ and $R^2$ independently is hydrogen, a $C_{1-8}$ alkyl group, a $C_{2-8}$ alkenyl group, a $C_{1-8}$ alkoxy group, a $C_{1-8}$ alkyl group having one to three halogen atoms, a $C_{1-8}$ alkoxy group having one to three halogen atoms, an aralkyl group consisting of a $C_{6-10}$ aryl moiety and a $C_{1-3}$ alkylene moiety, a halogen atom, hydroxyl, nitro, cyano, amino, a $C_{1-8}$ alkylamino group, a $C_{2-8}$ dialkylamino group, a $C_{2-8}$ acylamino group, a $C_{2-8}$ acylamino group having one to three halogen atoms, a $C_{1-8}$ alkylsulfonylamino group, carboxyl, a $C_{2-8}$ acyl group, an alkoxycarbonyl group comprising a $C_{1-8}$ alkoxy moiety, carbamoyl, a $C_{1-8}$ alkylthio group, a $C_{1-8}$ alkylsulfinyl group, a $C_{1-8}$ alkylsulfonyl group, or sulfamoyl;
$R^3$ is hydrogen, a $C_{1-8}$ alkyl group, a $C_{2-8}$ alkenyl group, a $C_{1-8}$ alkyl group having one to three halogen atoms, or an aralkyl group consisting of a $C_{6-10}$ aryl moiety and a $C_{1-3}$ alkylene moiety;
$R^4$ is hydrogen, a $C_{1-8}$ alkyl group, a $C_{2-8}$ alkenyl group, a $C_{1-8}$ alkoxy group, a $C_{1-8}$ alkyl group having one to three halogen atoms, a $C_{1-8}$ alkoxy group having one to three halogen atoms, an aralkyl group consisting of a $C_{6-10}$ aryl moiety and a $C_{1-3}$ alkylene moiety, a $C_{1-8}$ alkyl group having hydroxyl, a halogen atom, hydroxyl, nitro, cyano, amino, a $C_{1-8}$ alkylamino group, a $C_{1-5}$ alkylamino group having one to five halogen atoms, a $C_{2-8}$ dialkylamino group, a $C_{2-8}$ acylamino group, a $C_{2-8}$ acylamino group having one to three halogen atoms, a $C_{1-8}$ alkylsulfonylamino group, benzenesulfonylamino optionally having one or more substituents, carboxyl, a $C_{2-8}$ acyl group, an alkoxycarbonyl group comprising a $C_{1-8}$ alkoxy moiety, carbamoyl, a $C_{1-8}$ alkylthio group, a $C_{1-8}$ alkylsulfinyl group, a $C_{1-8}$ alkylsulfonyl group, sulfamoyl, phenyl optionally having one or more substituents, or a heterocyclic group optionally having one or more substituents;
the ring shown below is a five-membered to eight-membered ring optionally comprising one or two nitrogen atoms as the members of the ring, and being condensed with the benzene ring at the positions of 1 and 2 of the benzene ring; and

the ring shown below is an aromatic ring selected from the group consisting of benzene ring, naphthalene ring, pyridine ring, pyrimidine ring, quinoline ring, indole ring, indoline ring, benzimidazole ring, pyrazole ring, indazole ring, benzisoxazole ring, and benzotriazole ring,

provided that $R^4$ is neither hydrogen, a $C_{1-8}$ alkyl group, nor a halogen atom in the case that the ring shown below is benzene ring

2. A compound or a pharmacologically acceptable salt thereof defined in claim 1, wherein each of $R^1$ and $R^2$ independently is hydrogen, a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, or amino.

3. A compound or a pharmacologically acceptable salt thereof defined in claim 1, wherein $R^3$ is hydrogen or a $C_{1-8}$ alkyl group.

4. A compound or a pharmacologically acceptable salt thereof defined in claim 1, wherein $R^4$ is hydrogen, a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, a $C_{1-8}$ alkyl group having hydroxyl, a halogen atom, hydroxyl, cyano, amino, a $C_{1-8}$ alkylamino group, a $C_{2-8}$ dialkylamino group, a $C_{1-8}$ alkylsulfonylamino group, benzenesulfonylamino optionally having one or more substituents, phenyl optionally having one or more substituents, or a heterocyclic group optionally having one or more substituents.

5. A compound or a pharmacologically acceptable salt thereof defined in claim 1, wherein $R^4$ is a heterocyclic group optionally having one or More substituents, said heterocyclic group being tetrazolyl, triazolyl, pyridyl, imidazolyl, oxazolyl, or triazolyl, and said substituents being selected from the group consisting of a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, amino, a $C_{1-8}$ alkylamino group, and a $C_{2-8}$ dialkylamino group.

6. A compound or a pharmacologically acceptable salt thereof defined in claim 1, wherein $R^4$ is a $C_{1-8}$ alkoxy group, a $C_{1-8}$ alkyl group having one to three halogen atoms, a $C_{1-8}$ alkoxy group having one to three halogen atoms, hydroxyl, cyano, amino, a $C_{1-8}$ alkylamino group, a $C_{2-8}$ dialkylamino group, or benzenesulfonylamino optionally having one or more substituents, said substituents being selected from the group consisting of a $C_{1-8}$ alkyl group, a $C_{1-8}$ alkoxy group, a halogen atom, and nitro.

7. A compound or a pharmacologically acceptable salt thereof defined in claim 1, wherein the ring shown below is naphthalene ring, tetrahydronaphthalene ring, or indan ring

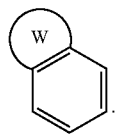

8. A compound or a pharmacologically acceptable salt thereof defined in claim 1, wherein the ring shown below is benzene ring or indole ring

9. A compound having the following formula (II) or a pharmacologically acceptable salt thereof:

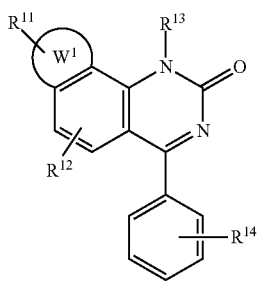

(II)

wherein each of $R^{11}$ and $R^{12}$ independently is hydrogen, a $C_{1-8}$ alkyl group, a $C_{2-8}$ alkenyl group, a $C_{1-8}$ alkoxy group, a $C_{1-8}$ alkyl group having one to three halogen atoms, a $C_{1-8}$ alkoxy group having one to three halogen atoms, an aralkyl group consisting of a $C_{6-10}$ aryl moiety and a $C_{1-3}$ alkylene moiety, a halogen atom, hydroxyl, nitro, cyano, amino, a $C_{1-8}$ alkylamino group, a $C_{2-8}$ dialkylamino group, a $C_{2-8}$ acylamino group, a $C_{2-8}$ acylamino group having one to three halogen atoms, a $C_{1-8}$ alkylsulfonylamino group, carboxyl, a $C_{2-8}$ acyl group, an alkoxycarbonyl group comprising a $C_{1-8}$ alkoxy moiety, carbamoyl, a $C_{1-8}$ alkylthio group, a $C_{1-8}$ alkylsulfinyl group, or a $C_{1-8}$ alkylsulfonyl group, or sulfamoyl;

$R^{13}$ is hydrogen, a $C_{1-8}$ alkyl group, a $C_{2-8}$ alkenyl group, a $C_{1-8}$ alkyl group having one to three halogen atoms, or an aralkyl group consisting of a $C_{6-10}$ aryl moiety and a $C_{1-3}$ alkylene moiety;

$R^{14}$ is a $C_{2-8}$ alkenyl group, a $C_{1-8}$ alkoxy group, a $C_{1-8}$ alkyl group having one to three halogen atoms, a $C_{1-8}$ alkoxy group having one to three halogen atoms, an aralkyl group consisting of a $C_{6-10}$ aryl moiety and a $C_{1-3}$ alkylene moiety, a $C_{1-8}$ alkyl group having hydroxyl, hydroxyl, nitro, cyano, amino, a $C_{1-8}$ alkylamino group, a $C_{1-5}$ alkylamino group having one to five halogen atoms, a $C_{2-8}$ dialkylamino group, a $C_{2-8}$ acylamino group, a $C_{2-8}$ acylamino group having one to three halogen atoms, a $C_{1-8}$ alkylsulfonylamino group, benzenesulfonylamino optionally having one or more substituents, carboxyl, a $C_{2-8}$ acyl group, an alkoxycarbonyl group comprising a $C_{1-8}$ alkoxy moiety, carbamoyl, a $C_{1-8}$ alkylthio group, a $C_{1-8}$ alkylsulfinyl group, a $C_{1-8}$ alkylsulfonyl group, sulfamoyl, phenyl optionally having one or more substituents, or a heterocyclic group optionally having one or more substituents; and the ring shown below is naphthalene ring, tetrahydronaphthalene ring, or indan ring

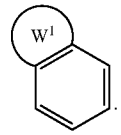

10. A compound or a pharmacologically acceptable salt thereof defined in claim 9, wherein each of $R^{11}$ and $R^{12}$ independently is hydrogen, a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, or amino.

11. A compound or a pharmacologically acceptable salt thereof defined in claim 9, wherein $R^{13}$ is hydrogen.

12. A compound or a pharmacologically acceptable salt thereof defined in claim 9, wherein $R^{14}$ is a $C_{1-8}$ alkoxy group, a $C_{1-8}$ alkyl group having one to three halogen atoms, a $C_{1-8}$ alkoxy group having one to three halogen atoms, a $C_{1-8}$ alkyl group having hydroxyl, hydroxyl, cyano, amino, a $C_{1-8}$ alkylamino group, a $C_{2-8}$ dialkylamino group, a $C_{1-8}$ alkylsulfonylamino group, benzenesulfonylamino optionally having one or more substituents, phenyl optionally having one or more substituents, or a heterocyclic group optionally having one or more substituents.

13. A compound or a pharmacologically acceptable salt thereof defined in claim 9, wherein $R^{14}$ is a heterocyclic group optionally having one or more substituents, said heterocyclic group being tetrazolyl, triazolyl, pyridyl, imidazolyl, oxazolyl, or triazolyl, and said substituents being selected from the group consisting of a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, amino, a $C_{1-8}$ alkylamino group, and a $C_{2-8}$ dialkylamino group.

14. A compound or a pharmacologically acceptable salt thereof defined in claim 9, wherein $R^{14}$ is a $C_{1-8}$ alkoxy group, a $C_{1-8}$ alkyl group having one to three halogen atoms, a $C_{1-8}$ alkoxy group having one to three halogen atoms, hydroxyl, cyano, amino, a $C_{1-8}$ alkylamino group, a $C_{2-8}$ dialkylamino group, or benzenesulfonylamino optionally having one or more substituents, said substituents being selected from the group consisting of a $C_{1-8}$ alkyl group, a $C_{1-8}$ alkoxy group, a halogen atom, and nitro.

15. A compound or a pharmacologically acceptable salt thereof defined in claim 9, wherein the ring shown below is naphthalene ring

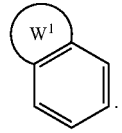

16. A P2X$_4$ receptor antagonist containing a compound or a pharmacologically acceptable salt thereof defined in claim 1, as an active ingredient.

17. A P2X$_4$ receptor antagonist containing a compound or a pharmacologically acceptable salt thereof defined in claim 9, as an active ingredient.

18. A therapeutic agent for neuropathic pain containing a compound or a pharmacologically acceptable salt thereof defined in claim 1, as an active ingredient.

19. A therapeutic agent for neuropathic pain containing a compound or a pharmacologically acceptable salt thereof defined in claim 9, as an active ingredient.

* * * * *